United States Patent
Noda et al.

(10) Patent No.: US 6,468,556 B1
(45) Date of Patent: Oct. 22, 2002

(54) LIVER FAT ACCUMULATION INHIBITORY COMPOSITION, FOOD ADDITIVE FOR LIVER FAT ACCUMULATION, INHIBITION, AND METHOD OF INHIBITING LIVER FAT ACCUMULATION

(75) Inventors: Tsuneyuki Noda, Kurume; Masamichi Toba, Tosu; Takuma Imada, Saga; Kyosuke Masaki, Sendai; Seiichi Shimizu, Otsu, all of (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/486,830

(22) PCT Filed: Aug. 31, 1998

(86) PCT No.: PCT/JP98/03911

§ 371 (c)(1),
(2), (4) Date: Mar. 3, 2000

(87) PCT Pub. No.: WO99/12538

PCT Pub. Date: Mar. 18, 1999

(30) Foreign Application Priority Data

Sep. 5, 1997 (JP) .............................................. 9-241061

(51) Int. Cl.⁷ ......................... A61K 47/00; A61K 31/22; A01N 37/06; A01N 37/00
(52) U.S. Cl. ....................... 424/439; 424/400; 424/484; 424/489; 514/549; 514/560; 514/893
(58) Field of Search ......................... 554/223; 424/439; 514/893, 560, 549

(56) References Cited

U.S. PATENT DOCUMENTS

| | | | |
|---|---|---|---|
| 5,436,269 A | * | 7/1995 | Yazawa et al. ............. 514/547 |
| 5,554,646 A | * | 9/1996 | Cook et al. ................. 514/560 |
| 5,837,733 A | * | 11/1998 | Pariza et al. ................ 514/560 |

FOREIGN PATENT DOCUMENTS

| | | |
|---|---|---|
| EP | 0 261 814 | 3/1988 |
| EP | 0 490 561 | 6/1992 |
| JP | 4-300828 | 10/1992 |
| JP | 9-194362 | 7/1997 |
| WO | WO 93/09772 | 5/1993 |
| WO | WO 94/16690 | 8/1994 |
| WO | WO 96/06605 | 3/1996 |
| WO | WO 96/22102 | 7/1996 |
| WO | WO 96/38137 | 12/1996 |
| WO | WO 97/46118 | 12/1997 |
| WO | WO 97/46230 | 12/1997 |
| WO | WO 98/37873 | 9/1998 |

OTHER PUBLICATIONS

"Linoleic Acid as a Mediator of Egg Size," Biosciences Information Service, Philadelphia, PA, vol. 69, No. 4, pp. 634–639 (Abstract Only).

"Preparation of Medicine of Treating Cardiovascular Diseases," Cent Hospital Zhengzhou, Jan. 17, 1996 (Abstract Only).

Y.L. Ha et al., "Anticarcinogens from Fried Ground Beef: Heat–Altered Derivatives of Linoleic Acid", Carcinogenesis, vol. 8, No. 12, pp. 1881–1887, (1987).

S.F. Chin et al., "Dietary Sources of Conjugated Dienoic Isomers of Linoleic Acid, a Newly Recognized Class of Anticarcinogens", Journal of Food Compositions and Analysis, vol. 5, pp. 185–197, (1992).

* cited by examiner

Primary Examiner—Thurman K. Page
Assistant Examiner—Charesse Evans
(74) Attorney, Agent, or Firm—Finnegan, Henderson, Farabow, Garrett & Dunner LLP

(57) ABSTRACT

A method of inhibiting liver fat accumulation which comprises administering a conjugated linoleic acid homolog to a mammal or making the mammal ingest it; and a liver fat accumulation inhibitory composition characterized by containing an effective amount of a conjugated linoleic acid homolog together with a support for medicinal preparations or foods. The administration or ingestion of CLA inhibits the total lipid content and the triglyceride content in the liver from increasing, and hence can effectively prevent diseases attributable to fatty liver, such as chronic hepatitis and hepatic cirrhosis.

4 Claims, No Drawings

LIVER FAT ACCUMULATION INHIBITORY COMPOSITION, FOOD ADDITIVE FOR LIVER FAT ACCUMULATION, INHIBITION, AND METHOD OF INHIBITING LIVER FAT ACCUMULATION

TECHNICAL FIELD

The present invention relates to a novel liver fat accumulation inhibitory composition, a food additive for liver fat accumulation inhibition, and a method of inhibiting liver fat accumulation.

BACKGROUND ART

It has been considered that fatty liver, which is a disease wherein fat is excessively accumulated in the liver (hepatocytes), is caused by supernutrition, hyperingestion of alcohol, diabetes and side effects due to administration of pharmaceuticals, and can cause severe diseases such as chronic hepatitis and hepatic cirrhosis. It is an important subject to treat and prevent fatty liver; however, there have not been accomplished any other safe and effective method for treatment and prevention thereof than control of nutrition to be fed, and there have scarcely been made any development of drugs (pharmaceuticals) for treatment and prevention.

Fatty liver refers to a state where lipid, particularly neutral fat, is accumulated in hepatocytes to the degree exceeding a physiologically permissible range, but a morphological/biochemical clear definition for a quantitative standard of fat deposition has still to be made. In general, fatty liver refers to a case where a remarkable morphological change in accumulation of neutral fat is recognized in hepatocytes over a range of a third of all lobuli and any other remarkable morphological abnormality can not be recognized. From a biochemical point of view, a standard for judgment of fatty liver is that the weight of neutral fat is about 10% (100 mg/g wet weight) or more of the wet weight of hepatic tissue.

An object of the present invention is to provide a novel composition capable of effectively preventing fatty liver, in its turn diseases such as chronic hepatitis and hepatic cirrhosis, by inhibiting hyperaccumulation of liver fat, and a method of inhibiting accumulation of liver fat.

DISCLOSURE OF THE INVENTION

To attain the above object, the present inventors have intensively studied and found that accumulation of liver fat is successfully inhibited by feeding or administering a conjugated linoleic acid. The present invention has been completed based on this novel knowledge.

That is, the present invention includes:

(1) a liver fat accumulation inhibitory composition characterized by containing an effective amount of a conjugated linoleic together with a support for medicinal preparations or foods;

(2) The liver fat accumulation inhibitory composition according to the item (1), wherein the conjugated linoleic acid is at least one selected from cis-9,trans-11-octadecadienoic acid, trans-10,cis-12-octadecadienoic acid, an isomer thereof, and an avirulent salt and ester thereof;

(3) The liver fat accumulation inhibitory composition according to the item (1) or (2), which is in the form of a food;

(4) The liver fat accumulation inhibitory composition according to the item (1) or (2), which is in the form of a pharmaceutical;

(5) A food additive for liver fat accumulation inhibition characterized by containing a conjugated linoleic acid as an active ingredient.

(6) A method of inhibiting liver fat accumulation, which comprises administering or feeding an effective amount of a conjugated linoleic acid to mammals; and (7) Use of a conjugated linoleic acid for preparation of a pharmaceutical composition or food additive for inhibiting liver fat accumulation.

According to the present invention, there can be provided a liver fat accumulation inhibitory composition, containing an effective amount of a conjugated linoleic acid (hereinafter referred to as "CLA") together with a support for medicinal preparations or foods; a food additive for liver fat accumulation inhibition, containing CLA as an active ingredient; and a method of inhibiting liver fat accumulation, using CLA.

More particularly, according to the present invention, there can be provided the above composition and additive, wherein CLA is at least one selected from cis-9,trans-11-octadecadienoic acid, trans-10,cis-12-octadecadienoic acid, an isomer thereof, and an avirulent salt and ester thereof; the above composition and additive, which are in the form of a food; the above composition and additive, which are in the form of a pharmaceutical; and a method of inhibiting liver fat accumulation, which comprises administering or feeding an effective amount of CLA to animals for subject.

Preferred composition of the present invention includes, for example, those containing CLA in the amount within a range from 0.2 to 90% (% by weight, the same rule applies correspondingly to the following) on a dry weight basis.

With the above constitution, accumulation of liver fat can be remarkably inhibited by feeding or administering the composition of the present invention. The reason is not clear at present, but is considered as follows. That is, since the amount of glutathione stored in the liver, which may be related to elimination of a free radical in the living body, shows significantly a high value, the capability of synthesizing glutathione is improved or consumption of glutathione is inhibited by feeding or administering CLA, thereby inhibiting liver fat accumulation. Any way, the present invention provides a novel composition or additive for inhibiting liver fat accumulation, or a novel method of inhibiting liver fat accumulation, which is very effective in the fields of pharmaceuticals and foods.

BEST MODE FOR CARRYING OUT THE INVENTION

It is essential that CLA as an active ingredient is incorporated into the composition of the present invention. CLA may be any of those contained in processed foods derived from ruminants, particularly dairy products such as yoghurt, and purified products and chemically synthesized products thereof. Details with respect to the method of producing CLA are described, for example, in literature of Ha, Y. L., et al., (Carcinogenesis, Vol. 8, 1881–1887 (1987)) and literature of Chin, S. F. et al., (Journal of Food Composition and Analysis, Vol. 5, 185–197 (1992)).

Preferred typical method includes, for example, a method of mixing linoleic acid or a natural supply source containing the same, more specifically corn oil, safflower oil or butter fat, with milk whey protein in almost the same amount and reacting the mixture at room temperature. CLA obtained by the method contains 9,11-octadecadienoic acid and/or 10,12-octadecadienic acid and an active isomer thereof. CLA can be used advantageously in the present invention in a free form (liquid), or in the form of an avirulent salt such as sodium salt or potassium salt, or an ester (e.g. methyl ester, ethyl ester, etc.) with a suitable alcohol such as methanol or ethanol, or in the form of a dry powder. 9,11-CLA and 10,12-CLA each including four geometric isomers such as cis,cis-, cis,trans-, trans,cis- and trans,trans-isomers, and all of these isomers can be used as the active ingredient of the composition of the present invention. CLA prepared from a supply source such as natural product is usually obtained as a mixture of these two or more isomers. In the present invention, CLA is generally used in the form of the mixture without being isolated, but can also be used after isolating according to a conventional procedure, as a matter of course.

The composition of the present invention is prepared in the form suited for feeding or administration by using a suitable support such as excipient or diluent in the same manner as in case of a conventional food composition or pharmaceutical, except that CLA is contained as the active ingredient.

The form of the food composition includes, for example, solid such as powder, granule, tablet, and block; aqueous solution such as beverage and soup; and liquid such as emulsion, dispersion, and suspension; and these forms are prepared by using suitable excipients, diluents and other edible substances according to a conventional procedure.

Nutrient resources such as protein, fat and carbohydrate are included in the support used herein. The protein includes, for example, casein and salts thereof, gelatin and salts thereof, water-soluble gelatin (e.g. enzymatically hydrolyzed gelatin, etc.), whole milk powder, skin milk powder, soybean protein, corn gluten meal, and wheat protein. The fat includes, for example, soybean oil, olive oil, middle-chain triglyceride (MCT), cottonseed oil, sunflower oil, cacao butter, sesame oil, rice oil, safflower oil, peanut oil, palm oil, and rapeseed oil. The carbohydrate includes, for example, monosaccharides such as dextrin, sucrose, fructose and glucose; disaccharides such as malt sugar, maltose; and oligosaccharides such as fracto-oligosaccharide, lacto-oligosaccharide, galactosyl lactose and lactosucrose.

The amount of the respective ingredients to be incorporated in the particularly preferred composition of the present invention is selected from the following range.

| Ingredients | Amount which can be incorporated (% by weight) | Preferred amount to be incorporated (% by weight) | Optimum amount to be incorporated (% by weight) |
| --- | --- | --- | --- |
| CLA | 0.1–90 | 0.5–60 | 1–25 |
| Protein | 10–65 | 40–65 | 40–53 |
| Fat | 5–90 | 5–80 | 10–18 |
| Carbohydrate | 15–70 | 15–40 | 20–35 |

The amount of the protein is expressed by the amount calculated on a pure content basis, which is determined by measuring the content of nitrogen in a raw material using a Kjeldahl method.

Furthermore, various known additives, which are usually added to this kind of food, can be optionally incorporated into the composition of the present invention. The additive includes, for example, various vitamins, minerals, perfumes such as synthetic perfume and natural perfume, natural sweeteners (e.g. thaumatin, stevia, etc.), synthetic sweeteners (e.g. saccharin, stevia extract, aspartame, etc.), colorants, flavors (e.g. cheese, chocolate, etc.) and dietary fibers such as polydextrose, pectic acid and salts thereof, and alginic acid and salts thereof. These additives can be used alone, or two or more kinds of them can be used in combination. The amount of these additives is not specifically limited, but is usually selected within a range from about 0 to 20 parts by weight based on 100 parts by weight of the composition of the present invention.

The composition of the present invention is prepared by mixing the above respective ingredients and the method of preparing the same is not specifically limited. However, there can be used a method of optionally adding an emulsifier (e.g. lecithin, sugar ester, etc.) and an auxiliary emulsifier (e.g. protein, carbohydrate, etc.), which are usually used, to a fat-soluble ingredient (e.g. fats and oils and other raw ingredients capable of dissolving in fats and oils, etc.) and mechanically emulsifying the mixture according to a conventional procedure, whereby the composition of the present invention can be prepared.

A product having storability can be obtained by packing a proper container with the composition of the present invention thus obtained (food of the present invention in the form of a liquid preparation) and subjecting to a retort sterilization treatment (120° C., 20 minutes). The product can be used as it is, or after being diluted appropriately.

The dose of the composition of the present invention thus prepared in the form of a beverage is appropriately selected according to the age, body weight and sex of mammals, particularly human, and the degree of liver fat accumulation, and is not specifically limited, but is preferably selected within a range from about 10 to 30 g per time on the dry weight basis or selected within a range from about 50 to 300 cc on the entire volume basis.

The composition of the present invention can also be applied into practical use after forming into the form of a general pharmaceutical preparation by using CLA as the active ingredient together with a suitable support for preparation. As the support for preparation, usually used diluents or excipients, for example, fillers, extenders, binders, humectants, disintegrators, surfactants and lubricants can be appropriately selected according to a dosage unit form of the preparation.

The dosage unit form of the pharmaceutical preparation can be selected from various forms according to the therapeutic purpose, and typical examples thereof include tablets, pills, powders, liquid preparations, suspensions, emulsions, granules, capsules, injections (e.g. liquid preparations, suspensions, etc.), ointments, and transfusion solutions.

When forming into the form of tablets, there can be used, as the support for preparation, excipients such as lactose, sucrose, sodium chloride, glucose, urea, starch, calcium carbonate, kaolin, crystalline cellulose, silicic acid, and potassium phosphate; binders such as water, ethanol, propanol, simple syrup, glucose solution, starch solution, gelatin solution, carboxymethylcellulose, hydroxypropylcellulose, methylcellulose, and polyvinyl pyrrolidone; disintegrators such as sodium carboxymethylcellulose, calcium carboxymethylcellulose, low substituted hydroxypropylcellulose, dry starch, sodium alginate, agar powder, laminaran powder, sodium hydrogencarbonate, and potassium carbonate; surfactants such as polyoxyethylene sorbitan fatty acid esters, sodium lauryl sulfate, and monoglyceride stearate; disintegration inhibitors such as sucrose, stearin, cacao butter, and hydrogenated oil; absorption accelerators such as quaternary ammonium base and sodium lauryl sulfate; humectants such as glycerin and starch; adsorbents such as starch, lactose, kaolin, bentonite, and colloidal silicic acid; and lubricants such as purified talc, stearate, powdered boric acid, and polyethylene glycol.

Furthermore, tablets can optionally take the form of normal coated tablets, for example, sugar-coated tablet, gelatin-coated tablet, enteric coated tablet, film-coated tablet, two-layer tablet, and multi-layer tablet.

When forming into the form of pills, for example, excipients such as glucose, lactose, starch, cacao butter, hardened vegetable oil, kaolin, and talc; binders such as powdered arabic gum, powdered tragacanth, gelatin, and ethanol; and disintegrators such as laminaran and agar can be used as the support for preparation.

When preparing in the form of injections and transfusion solutions, such as liquid, emulsion, and suspension, these injections and transfusion solutions are preferably sterilized and isotonic with blood. When forming into these forms, for example, water, ethyl alcohol, macrogol, propylene glycol, ethoxylated isostearyl alcohol, polyhydroxylated isostearyl alcohol, and polyoxyethylene sorbitan fatty acid esters can be used as the diluent. In this case, sodium chloride, glucose or glycerin may be contained in the composition of the present invention in the amount enough to prepare an isotonic solution and, furthermore, conventional solubilizing agents, buffers and soothing agents can also be added.

If necessary, colorants, preservatives, perfumes, flavors, sweeteners and other pharmaceuticals can also be contained in the pharmaceutical preparation.

When forming into the form of ointments such as paste, cream and gel, for example, white soft paraffin, paraffin, glycerin, cellulose derivative, polyethylene glycol, silicon, and bentonite can be used as the diluent.

The amount of CLA, as an active ingredient, to be contained in the composition of the present invention in the form of the pharmaceutical preparation thus prepared is not specifically limited and is appropriately selected from a wide range, but those containing about 10–90% CLA in a pharmaceutical preparation are preferred.

The method of administering the above pharmaceutical preparation is not specifically limited and is decided depending on various dosage forms, age, sex, other conditions of patients, and degree of the diseases. For example, tablets, pills, liquid preparations, suspensions, emulsions, granules and capsules are orally administered. Injections and transfusion solutions are intravenously administered as they are or after mixing with a conventional replenisher such as glucose and amino acid and, furthermore, they are intramuscularly, intracutaneously, subcutaneously or intraperitoneally injected as they are, if necessary.

The dose of the pharmaceutical preparation may be appropriately selected depending on the direction for use, age, sex, other conditions of patients, and degree of diseases of patients. The preparation can be administered 1 to 4 times per day with a daily dose (based on the compound of the present invention as the active ingredient) of about 0.5 to 20 mg/kg of body weight.

EXAMPLES

The present invention will be described in more detail by the following Preparation Examples of the composition of the present invention as Examples as well as Test Examples for clarifying the effect of inhibiting liver fat accumulation of the food composition containing the composition of the present invention. In the Examples and Test Examples, percentages are by weight unless otherwise stated.

Example 1

Soft capsules containing 300 mg or 500 mg of cis-9, trans-11-octadecadienoic acid were prepared.

Example 2

Compositions of the present invention in the form of a beverage were prepared by adding a predetermined amount of a protein ingredient, a carbohydrate ingredient, a CLA ingredient and other ingredients shown in Table 1 and Table 2 below to water.

The CLA ingredient is a CLA mixture in the form of a free fatty acid, which is commercially available from Nu-Chek-Prep, Inc. Compositions thereof are as follows.

| | |
|---|---|
| Cis-9,trans-11-CLA/trans-9,cis-11-CLA | 41% |
| Trans-10,cis-12-CLA | 44% |
| Cis-10,cis-12-CLA | 10% |
| Others | 5% |

TABLE 1

| | Formulation Example No. | | | | |
|---|---|---|---|---|---|
| | 1 | 2 | 3 | 4 | 5 |
| Content of protein (g/100 ml) | 5.2 | 6.8 | 5.7 | 5.0 | 5.6 |
| Content of carbohydrate (g/100 ml) | 15.0 | 15.5 | 11.9 | 12.6 | 9.8 |
| Content of lipid (g/100 ml) | 2.2 | 2.3 | 2.2 | 2.2 | 2.1 |
| Energy (kcal) | 100 | 110 | 90 | 90 | 80 |
| Protein ingredient | | | | | |
| Casein | 3.3 | 4.5 | — | — | — |
| Sodium caseinate | — | — | 2.2 | 2.6 | 3.3 |
| Calcium caseinate | — | — | 1.1 | 0.6 | — |
| Enzymaticlaly hydrolyzed casein | — | — | 0.7 | 2.2 | — |
| Enzymaticlaly hydrolyzed soybean protein | — | — | 0.2 | — | 0.5 |
| Enzymaticlaly hydrolyzed gelatin | 2.5 | 3.1 | 2.0 | — | 2.2 |
| Carbohydrate ingredient | | | | | |
| Dextrin | — | — | 8.4 | — | — |
| Maltotetraose syrup | 20.0 | 14.9 | — | 10.3 | — |
| Maltotriose syrup | — | 5.8 | 8.4 | — | 13.1 |
| Maltose syrup | — | — | — | 6.5 | — |
| CLA ingredient | 2.2 | 2.3 | 2.2 | 2.2 | 2.1 |
| Other ingredients | | | | | |
| Vitamin | q.s. | q.s. | q.s. | q.s. | q.s. |
| Mineral | q.s. | q.s. | q.s. | q.s. | q.s. |
| Perfume | q.s. | q.s. | q.s. | q.s. | q.s. |

TABLE 2

| | Formulation Example No. | | | | |
|---|---|---|---|---|---|
| | 6 | 7 | 8 | 9 | 10 |
| Content of protein (g/100 ml) | 6.9 | 5.0 | 3.5 | 5.1 | 5.0 |
| Content of carbohydrate (g/100 ml) | 3.0 | 8.7 | 17.0 | 12.6 | 8.7 |
| Content of lipid (g/100 ml) | 3.4 | 1.7 | 2.0 | 2.2 | 1.7 |
| Enerqy (kcal) | 70 | 70 | 100 | 90 | 70 |

TABLE 2-continued

| | Formulation Example No. | | | | |
|---|---|---|---|---|---|
| | 6 | 7 | 8 | 9 | 10 |
| Protein ingredient | | | | | |
| Casein | — | — | — | — | — |
| Sodium caseinate | 4.0 | 2.9 | 2.6 | 3.2 | 3.3 |
| Calcium caseinate | — | — | — | — | — |
| Enzymaticlaly hydrolyzed casein | 0.6 | 0.4 | 1.2 | — | — |
| Enzymaticlaly hydrolyzed soybean protein | 0.2 | — | — | 0.3 | — |
| Enzymaticlaly hydrolyzed gelatin | 2.6 | 2.1 | — | 2.0 | 2.1 |
| Carbohydrate ingredient | | | | | |
| Dextrin | 3.1 | — | — | — | 13.0 |
| Maltotetraose syrup | — | 6.0 | 22.7 | 16.8 | — |
| Maltotriose syrup | 1.3 | — | — | — | — |
| Maltose syrup | — | 5.6 | — | — | — |
| CLA ingredient | 3.4 | 1.7 | 2.0 | 2.3 | 1.7 |

TABLE 2-continued

| | Formulation Example No. | | | | |
|---|---|---|---|---|---|
| | 6 | 7 | 8 | 9 | 10 |
| Other ingredients | | | | | |
| Vitamin | q.s. | q.s. | q.s. | q.s. | q.s. |
| Mineral | q.s. | q.s. | q.s. | q.s. | q.s. |
| Perfume | q.s. | q.s. | q.s. | q.s. | q.s. |

Example 3

Compositions of the present invention in the form of a beverage were prepared by using an antioxidant vitamin, a CLA ingredient, an emulsifier, a medical oil, a carbohydrate ingredient, an organic acid, an oligosaccharide and other ingredients in each amount shown in Table 3 and Table 4 below. The CLA mixture in the CLA ingredient is the same as that shown in Example 2.

TABLE 3

| | Formulation Example No. | | | | | | | |
|---|---|---|---|---|---|---|---|---|
| | 1 | 2 | 3 | 4 | 5 | 6 | 7 | 8 |
| Antioxidant vitamin (mg/100 ml) | | | | | | | | |
| β-carotene | 1 | — | 3 | 5 | 30 | 0.3 | 1 | 1 |
| Extracted carotene | — | 1 | — | — | — | — | — | — |
| Ascorbic acid | 60 | 50 | 120 | 1000 | 100 | 20 | 60 | 30 |
| Vitamin E | — | — | 2 | 5 | — | — | — | 2 |
| CLA (mg/100 ml) | | | | | | | | |
| Cis-9, trans-11-CLA | 300 | 300 | 600 | 1000 | 500 | 100 | 300 | 300 |
| CLA mixture | — | — | — | — | — | — | — | — |
| Emulsifier (mg/100 ml) | q.s. | q.s. | q.s. | q.s. | q.s. | q.s. | q.s. | q.s. |
| Medical oil (mg/100 ml) | q.s. | q.s. | q.s. | q.s. | q.s. | q.s. | q.s. | q.s. |
| Carbohydrate ingredient | | | | | | | | |
| Isomerized sugar | — | — | — | 2 | — | — | — | — |
| Purified sucrose | — | — | — | 1 | — | — | — | 2 |
| Fructose | 7 | — | 7 | 4 | 5 | 2 | 8 | 8 |
| Glucose | — | 8 | 2 | — | 2 | — | 1 | — |
| Organic acid (mg/100 ml) | | | | | | | | |
| Citric acid | 500 | 600 | 600 | 200 | 500 | 200 | 400 | 400 |
| Tartaric acid | — | — | 200 | — | 100 | — | — | — |
| Malic acid | — | — | — | — | 100 | — | — | 100 |
| Fructo-oligosaccharide (g/100 ml) | — | — | — | — | — | 3 | — | 1 |
| Carbon dioxide gas (Vol) | — | — | — | — | — | — | 1 | 2 |
| Perfume and sweetener | q.s. | q.s. | q.s. | q.s. | q.s. | q.s. | q.s. | q.s. |

TABLE 4

| | Formulation Example No. | | | | | | | |
|---|---|---|---|---|---|---|---|---|
| | 9 | 10 | 11 | 12 | 13 | 14 | 15 | 16 |
| Antioxidant vitamin (mg/100 ml) | | | | | | | | |
| Lycopene | 1 | — | 3 | 5 | 30 | 0.3 | 1 | 1 |
| Lutein | — | 1 | — | — | — | — | — | — |
| Ascorbic acid | 60 | 50 | 120 | 1000 | 100 | 20 | 60 | 30 |
| Vitamin E | — | — | 2 | 5 | — | — | — | 2 |
| CLA (mg/100 ml) | | | | | | | | |
| Cis-9, trans-11-CLA | — | — | — | — | — | — | — | — |
| CLA mixture | 300 | 300 | 600 | 1000 | 500 | 100 | 300 | 300 |
| Emulsifier (mg/100 ml) | q.s. | q.s. | q.s. | q.s. | q.s. | q.s. | q.s. | q.s. |
| Medical oil (mg/100 ml) | q.s. | q.s. | q.s. | q.s. | q.s. | q.s. | q.s. | q.s. |

TABLE 4-continued

| | Formulation Example No. | | | | | | | |
|---|---|---|---|---|---|---|---|---|
| | 9 | 10 | 11 | 12 | 13 | 14 | 15 | 16 |
| Carbohydrate ingredients (g/100 ml) | | | | | | | | |
| Isomerized sugar | — | — | — | 2 | — | — | — | — |
| Purified sucrose | — | — | — | 1 | — | — | — | 2 |
| Fructose | 7 | — | 7 | 4 | 5 | 2 | 8 | 8 |
| Glucose | — | 8 | 2 | — | 2 | — | 1 | — |
| Organic acid (mg/100 ml) | | | | | | | | |
| Citric acid | 500 | 600 | 600 | 200 | 500 | 200 | 400 | 400 |
| Tartaric acid | — | — | 200 | — | 100 | — | — | — |
| Malic acid | — | — | — | — | 100 | — | — | 100 |
| Lactosucrose (g/100 ml) | — | — | — | — | — | 3 | — | 1 |
| Carbon dioxide gas (Vol) | — | — | — | — | — | — | 1 | 2 |
| Perfume and sweetener | q.s. | q.s. | q.s. | q.s. | q.s. | q.s. | q.s. | q.s. |

Test Example 1

In this test, using model rats with hereditary diabetes wherein obesity is developed about eighteen weeks after birth and fat is accumulated in the internal organs and liver, thereby to cause abnormality in glucose tolerance (OLETF rats, manufactured by OTSUKA PHARMACEUTICAL Co., Ltd.) and control rats (LETO rats, manufactured by OTSUKA PHARMACEUTICAL Co., Ltd.), an influence of ingestion of CLA on accumulation of fat in the liver of these rats was examined in the following procedure.

(1) Test animals and breeding

Five-week-old OLETF rats and LETO rats (see Japanese Laid-Open (Kokai) Patent Publication No. 4-252129) were subjected to the test after adaptation period of one week. The respective rats were divided into three groups below, each of which has eight rats, and then rats of each group were bred for eighteen weeks using diets shown below.
First group: control diet/LETO group
Second group: control diet/OLETF group
Third group: 0.5% CLA diet/OLETF group (2) Breeding The breeding temperature was controlled at 23±1° C.

A breeding room was illuminated from 7 a.m. to 7 p.m. Rats were allowed to feed freely. An AIN-76 purified diet (standard diet for rats in a growth period) was fed as a control diet and a diet prepared by adding CLA (concentration: 0.5%) to the control diet was fed, respectively. An average amount of the food intake per day is 28.06±1.96 g and, therefore, the amount of CLA intake per day in the third group was 0.14±001 g.

Rats were allowed to drink water freely during the test period. As CLA, CLA in the form of a free acid, which is available from Nu-Chek-Prep, Inc., was used. Compositions are as shown in Example 2 described above.

(3) Measurement of weight of lipid and amount of triglyceride

After the completion of the breeding, rats of the respective groups were sacrificed, followed by enucleation of the liver and further extraction of lipid of the liver, and then, the total weight of lipid was determined in accordance with a gravimetric method [method of Folch et al., i.e. Folch, J., Lee, M., and Sloane-Stanley, G. H., J. Biol. Chem. 226, 497–509 (1957)]. The amount of hepatic triglyceride was measured by using TRIGLYCERIDE TEST WAKO as a measuring kit manufactured by WAKO PURE CHEMICAL INDUSTRIES Co., Ltd. Analysis of glutathione (GSH) was effected by a HPLC method as modification of a method of TOYOOKA et al. [TOYOOKA, T. et al., Biomed. Chromatogr., 3, 166–172 (1989)].

(4) Results

The results are shown in Table 5 below.

TABLE 5

| Groups | Rat | Diet | Hepatic lipid (mg/g of liver) | Triglyceride | GSH ($\mu$mol/g of liver) |
|---|---|---|---|---|---|
| 1 | LETO | Control diet | 59.9 ± 2.4 | 9.4 ± 2.4 | 5.35 ± 1.21 |
| 2 | OLETF | Control diet | 162.0 ± 31.8 | 115.8 ± 33.9 | 4.61 ± 0.56 |
| 3 | OLETF | CLA diet | 98.2 ± 13.2 | 46.6 ± 12.3 | 5.69 ± 0.65 |

As is apparent from the above table, the OLETF rats as the model rat with hereditary diabetes showed a significantly high value in both of the total contents of lipid and triglyceride as compared with the LETO rats as the control rat in case of the ingestion of the same control diet. To the contrary, the OLETF rats to which a diet containing 0.5% CLA was fed showed a significantly low value in both of the total contents of lipid and triglyceride as compared with the OLETF rats to which a control diet was fed.

Any significant difference was not recognized in the consumption of the diet, body weight and weight of fat pad among the respective OLETF rats used as the third group. Therefore, an influence of an individual difference due to ingestion of CLA was not recognized.

Industrial Applicability

According to the present invention, hyperaccumulation of liver fat is inhibited by administering or feeding CLA to mammals. That is, a liver fat accumulation inhibitory composition, and a food additive for liver fat accumulation inhibition, each containing CAL, exhibit a remarkable effect of inhibiting liver fat accumulation. Therefore, according to the present invention, diseases derived from fatty liver, such as chronic hepatitis and hepatic cirrhosis, can be effectively prevented.

What is claimed is:

1. A method of inhibiting liver fat accumulation in mammals which comprises administering to a mammal a composition containing from about 0.5 to 20 mg/kg of body weight of the mammal of a conjugated linoleic acid to inhibit liver fat accumulation in the mammal.

2. The method of claim 1, wherein the conjugated linoleic acid is at least one selected from the group consisting of cis-9, trans-11-octadecadienoic acid, trans-10,cis-12-octadecadienoic acid, an isomer thereof, an avirulent salt thereof, and an ester thereof.

3. The method of claim 1 or 2, wherein the composition is in the form of a food.

4. The method of claim 1 or 2, wherein the composition is in the form of a pharmaceutical preparation.

* * * * *